(12) United States Patent
Currie et al.

(10) Patent No.: US 9,011,909 B2
(45) Date of Patent: Apr. 21, 2015

(54) PREBIOTIC SUPPOSITORIES

(75) Inventors: JoEllen Currie, Fox Point, WI (US); Jean M. Young, West Bend, WI (US); John Wundrock, West Bend, WI (US)

(73) Assignee: Wisconsin Pharmacal Company, LLC, Jackson, WI (US)

( * ) Notice: Subject to any disclaimer, the term of this patent is extended or adjusted under 35 U.S.C. 154(b) by 25 days.

(21) Appl. No.: 13/224,480

(22) Filed: Sep. 2, 2011

(65) Prior Publication Data

US 2012/0058181 A1  Mar. 8, 2012

Related U.S. Application Data

(60) Provisional application No. 61/379,865, filed on Sep. 3, 2010.

(51) Int. Cl.
| | | |
|---|---|---|
| A61K 9/64 | (2006.01) | |
| A61K 31/733 | (2006.01) | |
| A61K 9/00 | (2006.01) | |
| A61K 9/02 | (2006.01) | |
| A61K 9/20 | (2006.01) | |
| A61K 9/48 | (2006.01) | |
| A61K 31/702 | (2006.01) | |

(52) U.S. Cl.
CPC ............. *A61K 31/733* (2013.01); *A61K 9/0036* (2013.01); *A61K 9/02* (2013.01); *A61K 9/2054* (2013.01); *A61K 9/4866* (2013.01); *A61K 31/702* (2013.01)

(58) Field of Classification Search
None
See application file for complete search history.

(56) References Cited

U.S. PATENT DOCUMENTS

| | | | |
|---|---|---|---|
| 4,999,342 A * | 3/1991 | Ahmad et al. ................. | 514/54 |
| 5,902,743 A | 5/1999 | Luchansky et al. | |
| 5,922,375 A | 7/1999 | Luchansky et al. | |
| 6,348,589 B1 | 2/2002 | Pendergast et al. | |
| 6,645,506 B1 | 11/2003 | Farmer | |
| 6,706,287 B2 | 3/2004 | Ranganathan et al. | |
| 6,723,326 B1 | 4/2004 | Farmer | |
| 6,905,692 B2 | 6/2005 | Farmer | |
| 6,977,246 B2 | 12/2005 | Pendergast et al. | |
| 7,026,160 B2 | 4/2006 | Ranganathan | |
| 7,052,896 B2 | 5/2006 | Glenn et al. | |
| 7,101,565 B2 | 9/2006 | Monte | |
| 7,109,182 B2 | 9/2006 | Esnault et al. | |
| 7,125,708 B2 | 10/2006 | Wynne et al. | |
| 7,125,963 B2 * | 10/2006 | Naidu ........................... | 530/400 |
| 7,326,775 B2 | 2/2008 | Naidu | |
| 7,390,519 B2 | 6/2008 | Collins et al. | |
| 7,468,270 B2 | 12/2008 | Xaus Pey et al. | |
| 7,541,042 B2 | 6/2009 | Farmer | |
| 7,544,363 B2 | 6/2009 | Farmer | |
| 7,608,291 B2 | 10/2009 | Baillon et al. | |
| 7,807,185 B2 | 10/2010 | Farmer | |
| 2003/0003107 A1 | 1/2003 | Farmer | |
| 2003/0091549 A1 | 5/2003 | Collins et al. | |
| 2003/0092163 A1 | 5/2003 | Collins et al. | |
| 2003/0104076 A1 | 6/2003 | Berkulin et al. | |
| 2003/0113306 A1 | 6/2003 | Collins et al. | |
| 2003/0118571 A1 | 6/2003 | Reid et al. | |
| 2003/0138975 A1 | 7/2003 | Quirk | |
| 2004/0057943 A1 | 3/2004 | Xaus Pey et al. | |
| 2004/0105848 A1 | 6/2004 | Ranganathan | |
| 2004/0235788 A1 | 11/2004 | Mobasseri et al. | |
| 2004/0265291 A1 | 12/2004 | Drake et al. | |
| 2005/0026188 A1 | 2/2005 | Van Kessel et al. | |
| 2005/0220776 A1 | 10/2005 | Brondstad et al. | |
| 2006/0121015 A1 | 6/2006 | Collins et al. | |
| 2006/0165669 A1 | 7/2006 | Reid et al. | |
| 2006/0182708 A1 | 8/2006 | Bockmuhl et al. | |
| 2006/0251633 A1 | 11/2006 | Salvadori et al. | |
| 2006/0251635 A1 | 11/2006 | Glenn et al. | |
| 2006/0257375 A1 | 11/2006 | Ranganathan | |
| 2006/0269535 A1 | 11/2006 | Naidu et al. | |
| 2006/0270627 A1 | 11/2006 | Esnault et al. | |
| 2007/0026074 A1 * | 2/2007 | Martin et al. ................. | 424/488 |
| 2007/0116826 A1 | 5/2007 | Prakash et al. | |
| 2007/0253941 A1 | 11/2007 | Naidu et al. | |
| 2007/0275881 A1 | 11/2007 | Morrow et al. | |
| 2008/0050398 A1 | 2/2008 | Bockmuehl et al. | |
| 2008/0102061 A1 | 5/2008 | Sobol et al. | |
| 2008/0161234 A1 | 7/2008 | Andersch et al. | |
| 2008/0193428 A1 * | 8/2008 | Zhou et al. ................. | 424/93.45 |
| 2008/0199446 A1 | 8/2008 | Vriesema et al. | |
| 2008/0219961 A1 | 9/2008 | Rudolph et al. | |
| 2008/0226603 A1 | 9/2008 | Al-Ghazzewi et al. | |
| 2008/0261916 A1 | 10/2008 | Jaszberenyi et al. | |

(Continued)

FOREIGN PATENT DOCUMENTS

WO  2006/030100  3/2006

OTHER PUBLICATIONS

Garner, M. et al., "Comparative Study of Bacterial Utilisation of Oligosaccarides," International Dietary Fibre Conference, Vienna (Jul. 2009).
Roussseau, V. et al., "Prebiotic effects of oligosaccharides on selected vaginal lactobacilli and pathogenic microorganisms," *Anaerobe*, 11, pp. 145-153 (2005).
Buddington, K.K. et al., "Dietary Oligofructose and Inulin Protect Mice from Enteric and Systemic Pathogens and Tumor Inducers," *The Journal of Nutrition*, 132, pp. 472-477 (2002).
"Natural Remedy for Yeast Infection: Probiotics," http://web.archive. org/web/20091208042643/http://thecandidacleanse.org/candida-natural-home-remedies/natural-remedy-for-yeast-infection-probiotics/ (Dec. 8, 2009).
Tuohy, K.M. et al., "Modulation of the Human Gut Microflora Towards Improved Health Using Prebiotics—Assessment of Efficacy," *Current Pharmaceutical Design*, 11, pp. 75-90 (2005).
Web page featuring "Luvena Prebiotic," http://www.luvenacare. com/ (Feb. 2, 2011).
PCT, International Search Report and Written Opinion, International Application No. PCT/US2011/050305 (Jan. 17, 2012).

*Primary Examiner* — Snigdha Maewall
(74) *Attorney, Agent, or Firm* — Thompson Hine LLP

(57) ABSTRACT

A composition for vaginal insertion is in the form of a softgel, a two-part gelatin capsule, a tablet, or a suppository. The composition is designed to promote the growth of native vaginal flora, but does not promote the growth of *Gardenerella vaginalis* and *Candida albicans*. The composition includes a prebiotic in a pharmaceutically acceptable excipient and is essentially free of probiotics, lactoferrin, and plant extracts containing isoflavones.

20 Claims, 4 Drawing Sheets

(56) References Cited

U.S. PATENT DOCUMENTS

| | | |
|---|---|---|
| 2008/0299255 A1 | 12/2008 | Kim et al. |
| 2009/0005340 A1 | 1/2009 | Kristiansen |
| 2009/0035294 A1 | 2/2009 | Mahe et al. |
| 2009/0081167 A1 | 3/2009 | Mogna et al. |
| 2009/0088405 A1 | 4/2009 | Kehoe et al. |
| 2009/0092656 A1* | 4/2009 | Klamerus et al. ............ 424/433 |
| 2009/0117056 A1 | 5/2009 | Hodal et al. |
| 2009/0162323 A1 | 6/2009 | Boehm et al. |
| 2009/0163449 A1 | 6/2009 | Wempe |
| 2009/0202516 A1 | 8/2009 | Olmstead et al. |
| 2009/0220639 A1 | 9/2009 | Schmitt et al. |
| 2009/0221486 A1 | 9/2009 | Schmitt et al. |
| 2009/0238907 A1 | 9/2009 | Farmer |
| 2009/0258389 A1 | 10/2009 | Monsan et al. |
| 2011/0124594 A1 | 5/2011 | Bou Antoun |

\* cited by examiner

PREBIOTIC SUPPOSITORIES

RELATED APPLICATIONS

This application claims the benefit of U.S. Provisional Application No. 61/379,865, filed Sep. 3, 2010.

FIELD

This application relates to compositions comprising a prebiotic and, more particularly, to prebiotic suppository compositions.

BACKGROUND

Lactic acid-producing microorganisms (e.g., *Lactobacillus*) play an important role in the maintenance of healthy vaginal ecology. Some even believe that healthy vaginal ecology is primarily dependant upon specific, native lactic acid-producing microorganisms (e.g., lactobacilli). Some common lactobacilli strains found in the vagina include *Lactobacillus jensenii; Lactobacillus gasseri; Lactobacillus salivarius*; and *Lactobacillus casel*.

The specific composition of the microbiota has a major impact on vaginal health, as colonization of several undesirable organisms may result in bacterial vaginosis, candidiasis, or other diseases. Undesirable organisms include *Gardnerella, Candida*, and other opportunistic pathogens. Interestingly, colonization of these opportunistic pathogens appears to be far less common when the vaginal microbiota is well populated by lactobacilli.

Bacterial vaginosis is a microecologic condition in which there are dramatic alterations in the endogenous vaginal microflora. Specifically, bacterial vaginosis involves a reduction in the overall number of lactic acid-producing bacterial strains, with a concomitant multi-log population increase in a characteristic set of microflora including, but not limited to *Gardnerella vaginalis*, genital anaerobes, and mycoplasmas.

Bacterial vaginosis if left untreated can lead to potentially serious heath concerns for the woman and even an unborn child. Both observational and interventional studies have shown that bacterial vaginosis in the early stages of pregnancy is associated with pre-term delivery and, in later stages of gestation, miscarriage. These studies suggest that bacterial vaginosis may be a direct cause of adverse outcomes in pregnancy, rather than simply being a surrogate marker. Studies also suggest that ascending infection or abnormal lower reproductive tract microflora mediate adverse pregnancy outcomes.

Bacterial vaginosis can be mitigated by lactic acid producing (i.e., probiotic) organisms. As previously discussed, the cause-and-effect relationship in bacterial vaginosis is due to the reduction of lactic acid-producing bacterial strains with the resulting multi-log increases of anaerobic microorganisms including, but not limited to, *Gardnerella vaginalis*. However, the results of a recent 3900-woman study performed in Denmark demonstrated that absence of bacterial vaginosis was directly associated with sufficient vaginal colonization of aerobic lactic acid-producing organisms.

There have been attempts to develop products and/or methodologies that utilize hydrogen peroxide producing Lactobacilli as a vaginal suppository therapy for the amelioration of vaginal yeast infections, but viability of these microorganisms continues to be the main difficulty in the use of Lactobacilli in those formulations.

SUMMARY

Rather than try to supplement the flora of the vagina with additional lactic acid producing (i.e., probiotic) organisms, the present compositions are designed to promote growth of existing native vaginal flora to prevent a reduction in the overall number of lactic-acid producing bacterial strains. To accomplish this, the compositions disclosed herein include a prebiotic to promote the growth of at least some strains of vaginal lactobacilli (e.g., *Lactobacillus gasseri* and vaginal *Lactobacillus crispatus*) without promoting growth of *Gardnerella vaginalis* and *Candida albicans* strains. Accordingly, the prebiotics would be selectively fermented by lactobacilli but not by competing opportunistic pathogens. Thus, the composition preferentially enhances the growth and colonization of the lactobacilli population in the vagina, which thereby helps reduce the incidence of vaginal disease.

In one aspect, vaginal suppositories are disclosed that promote the growth of native vaginal flora for healthy vaginal ecology. The vaginal suppositories include a prebiotic suspended in a suppository base by a suspending agent. The vaginal suppositories are essentially free of probiotic, lactoferrin, and plant extracts containing isoflavones and may also include a preservative and a pH adjuster. The prebiotic is preferably a bifidogenic oligosaccharide such as a fructo-oligosaccharide, a galacto-oligosaccharide, an inulin, an iso-malto-oligosaccharide, a lactulose, a soy-oligosaccharide, a xylo-oligosaccharide, and combinations thereof. In one embodiment, the bifidogenic oligosaccharides include a fructo-oligosaccharide, preferably a short-chain fructo-oligosaccharide derived from beets or sugar cane.

In one embodiment, the vaginal suppository composition includes a prebiotic at about 0.25-75% by weight, a suspending agent at about 0.2-2.0% by weight with the balance being suppository base. This composition may also include a preservative at about 0.1-0.18% by weight of the composition, the preservative comprising methylparaben, and lactic acid at about 0.01-0.04% by weight of the composition to keep the prebiotic from hydrolyzing into simple sugars. In another embodiment, the vaginal suppository composition includes a prebiotic at about 2.0-10% by weight, a suspending agent at about 0.5-1.5% by weight with the balance being suppository base. For either embodiment, the suspending agent may be or includes silicon dioxide, and the suppository base may be or includes polyethylene glycol.

In another aspect, a vaginal suppository composition includes polyethylene glycol at about 97% by weight, a preservative at about 0.1% by weight, a fructo-oligosaccharide at about 2% by weight, a suspending agent at about 0.8% by weight, and a pH adjuster at about 0.03% by weight of the composition with the fructo-oligosaccharide suspended by the suspending agent in the polyethylene glycol. In one embodiment, the polyethylene glycol includes a mixture of polyethylene glycol 1000 and polyethylene glycol 1450, the preservative includes methylparaben, the suspending agent includes silicon dioxide, and the pH adjuster includes lactic acid.

In another aspect, a composition for vaginal insertion includes a prebiotic in a pharmaceutically acceptable excipient and that is essentially free of probiotics. The prebiotic may be a liquid or a powder fructo-oligosaccharide. In one embodiment, the composition is housed within a softgel and the fructo-oligosaccharide is a liquid. In another embodiment, the composition is housed within a two-part gelatin capsule and the fructo-oligosaccharide is a powder. In another embodiment the excipient is a tabletting excipient and the composition is in tablet form.

In another aspect, methods of promoting the growth of native vaginal flora are disclosed. The method includes inserting any of the vaginal suppository compositions described above into a vagina and allowing sufficient time for at least some strains of vaginal *Lactobacillus gasseri* and vaginal *Lactobacillus crispatus* to grow without allowing strains of *Gardnerella vaginalis* and *Candida albicans* to grow. As such, the prebiotic composition strengthens the native lactobacilli population, thereby promoting an environment hostile to vaginal pathogens—thereby promoting vaginal health maintenance and acting as an infection preventative.

The features, functions, and advantages that have been discussed can be achieved independently in various embodiments or may be combined in yet other embodiments, further details of which can be seen with reference to the following drawings and description.

DESCRIPTION

Figure 1:
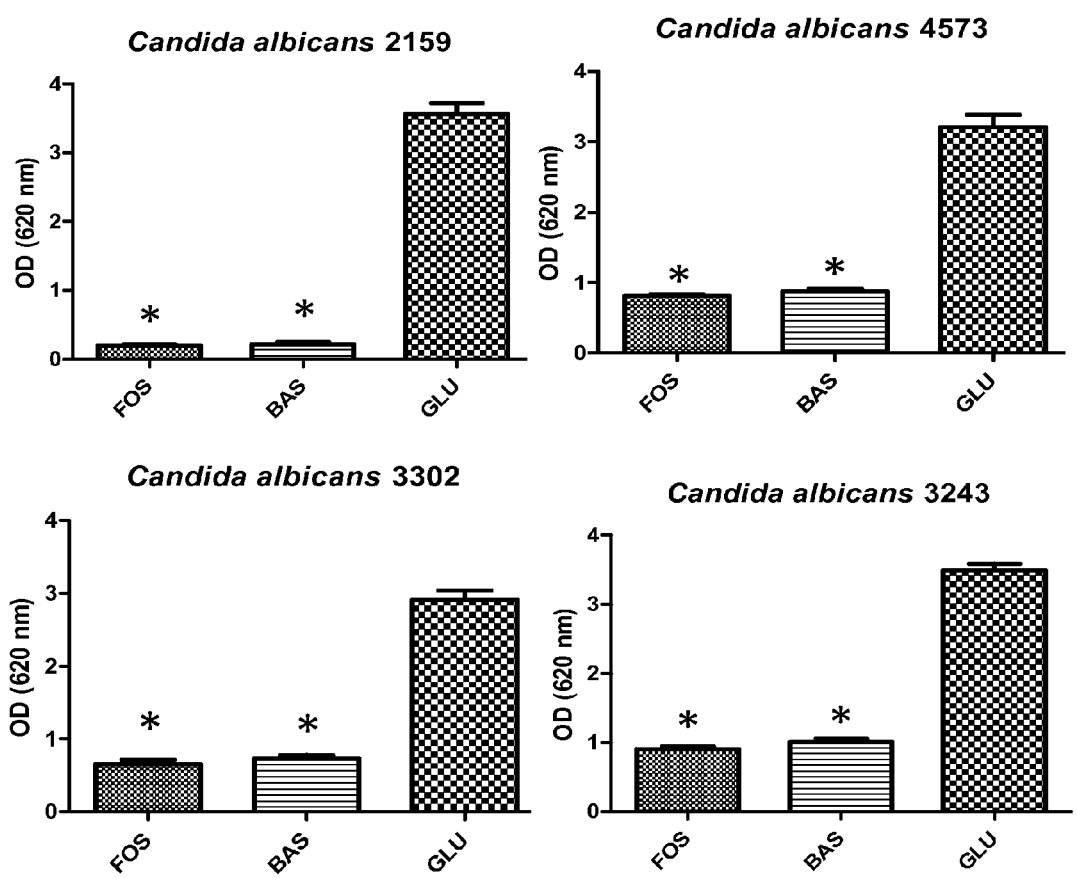
FIG. 1 contains four graphs showing that various strains of vaginal *Candida albicans* do not grow in the presence of fructo-oligosaccharide.

Vaginal suppositories that promote the growth of native vaginal flora for healthy vaginal ecology are disclosed herein. The suppositories can take any of a variety of forms, such as a solidified plug, a softgel capsule, a two-part gelatin capsule, or a tablet. The vaginal suppositories may include a composition essentially free of probiotics and comprising a prebiotic in a pharmaceutically acceptable excipient.

As used herein "essentially free of probiotics" may mean that the composition includes less than 0.08% by weight of a probiotic, more preferably less than about 0.01% by weight of a probiotic, and may contain no probiotics.

Suitable prebiotics promote the growth of at least some strains of vaginal lactobacilli without significantly promoting growth of adverse microorganisms, such as at least *Gardnerella vaginalis* and/or *Candida albicans* strains. Accordingly, the prebiotic selectively feeds the lactobacilli thereby enhancing its growth and colonization in the vagina, which is believed to reduce the incidence of vaginal disease. The prebiotic may include a bifidogenic oligosaccharide such as one or more of a fructo-oligosaccharide, inulin (available from any number of sources including, but not limited to chicory, onion, garlic, Jerusalem artichoke, asparagus, tomato and banana), a lactulose, a galacto-oligosaccharide, an isomalto-oligosaccharide, a soy-oligosaccharide, and a xylo-oligosaccharide.

The prebiotics may be from about 0.25% by weight to about 75% by weight of the composition, more particularly from about 2.0% by weight to about 10% by weight thereof. In one embodiment, the prebiotic includes a fructo-oligosaccharide. The fructo-oligosaccharide may be a short-chain fructo-oligosaccharide derived from beet or sugar cane. One preferred short-chain fructo-oligosaccharide (scFOS®) in powder form is NutraFlora® P-95 available from GTC Nutrition, Golden, Colo., which is derived from cane sugar. NutraFlora® P-95 contains, on a dry basis, more than 95% fructo-oligosaccharides (comprised of 50% GF3, 35% GF2, and 10% t GF4), less than 5% glucose, fructose, and sucrose, less than 5% moisture, and less than 0.1% ash.

In one embodiment, the vaginal suppositories include the prebiotic suspended in a suppository base by a suspending agent and are essentially free of probiotics. The compositions may also include a preservative and a pH adjuster. The prebiotic may include a bifidogenic oligosaccharide. In one embodiment, the bifidogenic oligosaccharide is a fructo-oligosaccharide, such as a short-chain fructo-oligosaccharide.

Suitable suppository bases include excipients that are solid at room temperature and melt at about average core body temperature of about 98.6° F. or at about 94° F. to about 100° F. Such excipients, include, but are not limited to, one or more of polyethylene glycol, hydrogenated vegetable oils, cocoa butter, Theobroma oil, hydrogenated corn oil, palm oil, palm kernel oil, and coconut oil. Some commercially available suppository bases include Hydrokote® M and Hydrokote® 122 hydrogenated vegetable oils from Abitec Corporation, Columbus, Ohio and Wecobee® M, Wecobee® S, and Wecobee® FS hydrogenated vegetable oils from Stepan Company, Northfield, Ill. Both manufacturers supply different melting point materials. Accordingly, mixtures of the various melting point materials enable the development of a composition that will best suit vaginal application by having a melting point at about average core body temperature. In one embodiment, the hydrogenated oils can be used at a percentage of 50%-90% by weight as an oil base for a suppository. The percentages can be mixed and matched to obtain the desired melting point for the product.

In another embodiment, polyethylene glycol (PEG) is used as a suppository base. A water-soluble polyethylene glycol base is preferred because it does not result in an oily discharge. Polyethylene glycols of various molecular weights are known and, based on the molecular weight, will have different melting points. Accordingly, mixtures of the various melting point polyethylene glycols enable the development of a composition that will best suit vaginal application by having a melting point at about average core body temperature (taken internally) of 98.6° F. or at about 94° F. to about 100° F. In one embodiment, two different molecular weights of PEG (PEG 1000 and PEG 1450) are combined to obtain the best melting point for the intended application. The PEG 1000 may be present as about 5% to about 95% by weight of the mixture and PEG 1450 may be present as about 5% to about 90% by weight of the mixture. In another embodiment, PEG 1000 may be present as about 75% to about 95% and the PEG 1450 may be present as about 10% to about 25% by weight of the mixture.

Any pharmaceutically acceptable inorganic suspending agent that keeps the prebiotic from settling out of the composition may be used to suspend the prebiotic in the suppository base. Non-limiting illustrative examples of suitable inorganic suspending agents include silicon dioxide, bentonite, hydrated aluminum silicate (e.g. kaolin) and mixtures thereof. Silicon dioxide is a particularly useful inorganic suspending agent. The silicon dioxide may be a fumed silicon dioxide. In one embodiment, the silicon dioxide is mixed with any other dry ingredients before being added to the suppository base, such as when the suppository base is molten. The suspending agent may be present in the composition as about 0.2% to about 2.0% by weight. In one embodiment, the suspending agent is 0.8% by weight of the composition.

Non-limiting illustrative examples of suitable preservatives include methylparaben, propylparaben, potassium sorbate, benzalkonium chloride, and benzethonium chloride, of which one or more may be present in the vaginal suppository compositions. In one embodiment, the preservative includes methylparaben as about 0.1% to about 0.18% by weight of the composition. In another embodiment, the preservative includes methylparaben as about 0.1% by weight of the composition. One of skill in the art will appreciate that the preservative is present for its affect on the suppository composition. For example, if the product is removed from its wrapper and handled, and then not used, the preservative is intended to keep the product from growing bacteria, and if bacteria are somehow introduced, the preservative is intended to keep the bacteria from thriving. In another embodiment, the preservative includes propylparaben as about 0.02% to about 0.1% by weight of the composition. In another embodiment, the preservative includes potassium sorbate as about 0.1% to about 0.2% by weight of the composition. In another embodiment, the preservative includes benzalkonium chloride as about 0.01% to about 0.02% by weight of the composition. In another embodiment, the preservative includes benzethonium chloride as about 0.01% to about 0.02% by weight of the composition.

The vaginal suppository compositions may also include a pH adjuster. A pharmaceutically acceptable pH adjuster may be used. The pH adjuster may be an acid, base, or buffer. In one embodiment, the pH adjuster is an acid, preferably lactic acid. The acid is added to adjust the pH of the composition to the pH at which the prebiotic is most stable, i.e., the prebiotic is prevented from hydrolyzing into simple sugars. In one embodiment, the prebiotic includes a fructo-oligosaccharide and as such the pH is adjusted to a pH>4.0. In an embodiment containing the fructo-oligosaccharide at about 2% to about 10% by weight, lactic acid may be added as about 0.01% to about 0.04% by weight of the composition to adjust the pH to a pH>4.0.

In one embodiment, the vaginal composition includes polyethylene glycol at about 97% by weight, a preservative at about 0.1% by weight, a fructo-oligosaccharide at about 2% by weight, a suspending agent at about 0.8% by weight, and a pH adjuster at about 0.03% by weight with the fructo-oligosaccharide suspended in the polyethylene glycol by the suspending agent. The preservative may include methylparaben, the suspending agent may include silicon dioxide, the pH adjuster may include lactic acid, and the polyethylene glycol may be about a 4.7:1 blend of PEG 1000 and PEG 1450.

In another embodiment, a suppository formulation includes hydrogenated vegetable oil and cocoa butter. The hydrogenated vegetable oil may comprise 75-95% by weight of the composition. The cocoa butter may comprise 4-25% by weight of the composition. The suppository formulation, combined with the hydrogenated vegetable oil and cocoa butter, may include the following: tocopheryl acetate (vitamin E) (0.2-2.5% by weight), methylparaben (0.02-0.2% by weight), propylparaben (0.02-0.15% by weight), a weak acid (0.01-0.05% by weight), fumed silica (0.02-2%), FOS (0.5-5.0% by weight), and, optionally, glyceryl monostearate (1-8%).

The compositions discussed above may be essentially free of certain additional substances. A composition that is essentially free of a substance may contain a small percentage thereof, and that percentage varies with the substance. In one embodiment, the composition is essentially free of lactoferrin as seen in the Examples provided below. "Essentially free of lactoferrin" as used herein means that the composition contains less than 0.000001 mg/ml or no lactoferrin. The composition that is essentially free of lactoferrin may also be essentially free of glycogen, lactoperoxidase, and lysozyme.

In another embodiment, the compositions may be essentially free of plant extracts that contain isoflavone. As used herein "essentially free of plant extracts that contain isoflavones" means that a composition contains less than about 0.2%, about 0.15%, or about 0.1%, or about 0.5% thereof. Of course, the composition may be completely free of plant extracts that contain isoflavones.

The vaginal suppositories described above as having a prebiotic suspended in a suppository base may be manufactured by melting the suppository base in a hot box for several days and then mixing the suppository base with the other ingredients. In one embodiment, wherein two or more materials are being mixed to form the suppository base, each is melted separately and then the molten suppository bases are weighed and measured into a mixing vessel, where the plurality of suppository bases are blended together with constant agitation.

Next, the preservative is dissolved in the molten mixture of suppository bases. The temperature is monitored closely so as not to reach a temperature that will compromise the prebiotic. The prebiotic and combined suspending agent, typically as a powder mixture, are then added to the molten suppository base and are mixed therein. After 30 minutes, the pH adjuster is added to adjust the pH of the composition and samples may be taken and tested. The molten final composition may be stored in a hotbox until filled on a suppository filling machine. Otherwise, the molten composition may be fed directly into a suppository filling machine.

Each suppository produced during the filling process may be about 1.9 to 2.1 grams. The suppositories may be filled into foil strips, plastic strips, or the like that have a plurality of the suppositories per strip. In one embodiment, there may be five suppositories per strip that are thereafter packaged as three strips per box. The box may contain any desired number of suppositories made from any number of suppositories per strip and any number of strips. Three strips of five suppositories is merely one option. The box may also include an applicator. Alternately, the suppositories may be individually wrapped or packaged and placed into jars rather than boxes. The jar may include an applicator therein or removeably attached thereto. One of skill in the art will appreciate that these are non-limiting examples of various ways to package a kit of vaginal suppositories having compositions as disclosed herein and an applicator.

In another embodiment, the vaginal suppositories include a composition essentially free of probiotics and having a prebiotic in a pharmaceutically acceptable excipient. The composition may be housed within a softgel. A softgel is a gelatin based shell surrounding a liquid fill, and is typically filled using encapsulation processes known to one of skill in the relevant arts. The softgel shell may be a combination of gelatin, water, and a plasticizer such as glycerin and/or sorbitol(s) or other polymer such as starch and carrageenan rather than gelatin. The prebiotic may be any of those disclosed above. In one embodiment, the softgel shell is a gelatin and the prebiotic includes a fructo-oligosaccharide, preferably a short-chain fructo-oligosaccharide such as NutraFlora® FOS available in a concentrated liquid form. The gelatin may be from an animal or vegetable.

The softgel capsules may be any available capsules such as a beef soft gel or a vegetarian softgel. In one embodiment, the liquid formulation prepared to fill the softgels includes propylene glycol (25-50% by weight), polyethylene glycol (26-60% by weight), glycerin (5-15% by weight), methylparaben (0.8-20% by weight), fumed silica (0.02-2.0% by weight), a weak acid (0.1-0.5% by weight), and FOS (0.5-5.0% by weight).

The softgels may be packaged in a foil-backed blister package to keep the softgels isolated from ambient moisture. The softgels may be packaged in a kit comprising a plurality of the softgels and an applicator.

In another embodiment, the composition may be housed within a two-part gelatin capsule. Commercially available gelatin capsules may be used, but if the capsules will not melt at about the average core body temperature of 98.6° F. or at about 94° F. to about 100° F., then gelatin capsules may be made using known techniques to have the desired melting point. The prebiotic may be any of those disclosed above. In one embodiment, the prebiotic includes a powder fructo-oligosaccharide, such as a short-chain fructo-oligosaccharide, mixed with an excipient such as rice flour. The rice flour is present in an amount to provide a desired concentration of the prebiotic, e.g., about 2% to about 10% by weight. In one embodiment, this powder mixture also includes a flow agent to aid the powder in flowing into the capsules during the filling process. The flow agent may be silicon dioxide or microcrystalline cellulose.

The hard gelatin capsules may be any available capsules such as a bovine or a vegetarian capsule. In one embodiment, the formulation prepared to fill the capsules includes calcium phosphate (5-25% by weight), magnesium stearate (0.5-2.5% by weight), rice flour or corn starch (5.0-90% by weight), silicon dioxide (0.1-4% by weight), a weak acid (0.01-2.% by weight), and FOS (1.0-99.% by weight).

The gelatin capsules may be packaged in a foil-backed blister package to keep them isolated from ambient moisture and may be packaged in a kit comprising a plurality of the capsules and an applicator.

In another embodiment, the vaginal suppositories include a composition essentially free of probiotics and having a prebiotic in a pharmaceutically acceptable tabletting excipient. The composition may be formed into a tablet. The tablet may be formed using tabletting processes known to one of skill in the art. The prebiotic may be any of those disclosed above. In one embodiment, the prebiotic includes a powder fructo-oligosaccharide, preferably a short-chain fructo-oligosaccharide, and the tabletting excipient is one or more of dicalcium phosphate, magnesium stearate, talc, microcrystalline cellulose, corn starch, stearic acid, calcium carbonate, and hypromellose. A sugar-based tabletting excipient should only be used if it will not encourage the growth of adverse bacteria. The tabletting excipient is preferably present in an amount to provide a desired concentration of the prebiotic, e.g., about 2% to about 10% by weight. Citric acid or ascorbic acid can be added to adjust the acidity of the product to best suit the vaginal application.

In one embodiment, a tablet formulation includes microcrystalline cellulose (5-15% by weight), dicalcium phosphate dihydrate (30-60% by weight), disintegrating agent (1-12% by weight), lubricating agent (0.5-2.5% by weight), fumed silica (0.1-2.0% by weight), a weak acid (0.05-0.5% by weight), and FOS (2-10% by weight).

In another embodiment, a tablet formulation includes lactose monohydrate (45-75%), hydroxypropyl methylcellulose (2-24%), microcrystalline cellulose (15-45% by weight), disintegrating agent (1-12% by weight), lubricating agent (0.2-2% by weight), fumed silica (0.1-2.0% by weight), a weak acid (0.05-0.5% by weight), and FOS (2-10% by weight).

The tablets may be packaged in a foil-backed blister package to keep them isolated from ambient moisture. The tablets may be packaged in a kit comprising a plurality of the tablets and an applicator.

Using any of the above vaginal suppositories, the growth of native vaginal flora is promoted by inserting a vaginal suppository into a vagina and allowing sufficient time therein for at least some strains of vaginal lactobacilli to grow. While enabling the *Lactobacillus* to grow, the vaginal suppositories have a composition that generally does not promote the growth of *Gardnerella vaginalis* and *Candida albicans*. Accordingly, this method by application of the prebiotic composition strengthens the native lactobacilli population, thereby promoting an environment hostile to vaginal pathogens—thereby promoting vaginal health maintenance and acting as an infection preventative.

In one embodiment, about five to eight hours is likely to be a sufficient time to allow some strains of vaginal lactobacilli to grow. The method may include inserting a vaginal suppository once daily, preferably at bed time.

Example 1

A vaginal suppository having the composition shown below in Table 1 was prepared by melting the polyethylene glycols separately in a hot box for several days. The molten polyethylene glycols were weighed and measured into a mixing vessel to provide the percent by weight reported below. With constant agitation, the polyethylene glycols were blended together.

The preservative was then dissolved in the blended polyethylene glycols. The temperature was monitored closely so as not reach a temperature that would compromise the fructo-oligosaccharides. With the polyethylene glycols at <137° F., the fructo-oligosaccharide and the silicon dioxide were added to the molten material and mixed. After 30 minutes, the lactic acid was added to reduce the acidity of the suppository.

The molten blend was stored in the hotbox until filled on a suppository filling machine.

TABLE 1

| Ingredient | Percentage w/w |
|---|---|
| Polyethylene Glycol 1000 NF | 80.00 |
| Polyethylene Glycol 1450NF | 17.07 |
| Methylparaben | 0.10 |
| short chain Fructo-oligosaccharide | 2.00 |
| Silicon dioxide | 0.80 |
| Lactic acid | 0.03 |

The vaginal suppositories promote the growth of at least some strains of vaginal *Lactobacillus gasseri* and vaginal *Lactobacillus crispatus* without promoting strains of *Gardnerella vaginalis* and *Candida albicans* to grow. This was demonstrated by the following tests.

Strains of the various bacteria, all of which were described as being isolated from the human vaginal tract, were obtained from public culture collections in the U.S. and Europe. The strains were grown on the following media: MRS broth for lactobacilli (except for *L. iners*), Yeast Peptone Dextrose (YPD) broth for *Candida*, and NYC-III broth (the medium recommended by ATCC) for *Gardnerella* and *L. iners*. For each, a basal medium was prepared without adding carbohydrate. For positive controls, glucose (2%) was added as the sole carbohydrate source, and for the FOS treatments, 2% FOS (NutraFlora® P95, obtained from GTC Nutrition, Golden, Colo.) was added. Because the FOS is only 95% pure and contains a small amount (5%) of sucrose, glucose, and fructose, a negative control containing the equivalent amount of these sugars (i.e., 2%×5%=0.1%) was added to the basal medium.

Cultures were incubated at 37° C. under appropriate atmospheric conditions, either ambient for most of the lactobacilli, ambient for *Candida*, or in a $CO_2$ incubator for *Gardnerella* and *L. iners*. Cell densities were determined spectrophotometrically by optical density measurement (OD at 620 nm). The pH before and after growth was determined using a pH electrode. All growth experiments were performed in duplicate and with two replications (n=4).

The strains tested and their resulting FOS fermentation/growth of each are provided below in Table 2.

TABLE 2

| STRAIN | SOURCE | MEDIUM | FOS fermentation/growth |
|---|---|---|---|
| *Lactobacillus reuteri* MV14-1a | UNL | MRS | Negative (−) |
| *Lactobacillus reuteri* Uga 4-1 | UNL | MRS | Negative (−) |
| *Lactobacillus reuteri* Uga 44-1 | UNL | MRS | Negative (−) |
| *Lactobacillus vaginalis* 12891 | BCCM/LMG | MRS | Negative (−) |
| *Lactobacillus vaginalis* 44134 | CCUG | MRS | Negative (−) |
| *Lactobacillus vaginalis* 44032 | CCUG | MRS | Negative (−) |
| *Lactobacillus vaginalis* 44123 | CCUG | MRS | Negative (−) |
| *Lactobacillus gasseri* 13134 | BCCM/LMG | MRS | Negative (−) |
| *Lactobacillus gasseri* 30386 | CCUG | MRS | Negative (−) |
| *Lactobacillus gasseri* 24836 | CCUG | MRS | Positive (+) |
| *Lactobacillus gasseri* 29472 | CCUG | MRS | Positive (+) |
| *Lactobacillus crispatus* 12009 | BCCM/LMG | MRS | Positive (+) |
| *Lactobacillus crispatus* 11440 | BCCM/LMG | MRS | Positive (+) |
| *Lactobacillus crispatus* 44015 | CCUG | MRS | Negative (−) |
| *Lactobacillus crispatus* 42897 | CCUG | MRS | Positive (+) |
| *Lactobacillus crispatus* 38700 | CCUG | MRS | Positive (+) |
| *Lactobacillus jensenii* 35572 | CCUG | MRS | Negative (−) |
| *Lactobacillus jensenii* 44149 | CCUG | MRS | Negative (−) |
| *Lactobacillus jensenii* 35573 | CCUG | MRS | Negative (−) |
| *Lactobacillus jensenii* 44492 | CCUG | MRS | Negative (−) |
| *Lactobacillus iners* 18916 | CCUG | NYC III | Negative (−) |
| *Lactobacillus iners* 27589 | CCUG | NYC III | Negative (−) |
| *Lactobacillus iners* 18913 | CCUG | NYC III | Negative (−) |
| *Gardnerella vaginalis* 49145 | ATCC | NYC III | Negative (−) |
| *Gardnerella vaginalis* 14018 | ATCC | NYC III | Negative (−) |
| *Gardnerella vaginalis* 14019 | ATCC | NYC III | Negative (−) |
| *Gardnerella vaginalis* 14325 | BCCM/LMG | NYC III | Negative (−) |
| *Candida albicans* 4573 | BCCM/IHEM | YPD | Negative (−) |
| *Candida albicans* 2159 | BCCM/IHEM | YPD | Negative (−) |
| *Candida albicans* 3302 | BCCM/IHEM | YPD | Negative (−) |
| *Candida albicans* 3243 | BCCM/IHEM | YPD | Negative (−) |

UNL = University of Nebraska-Lincoln Culture Collection
BCCM/LMG = Belgian Coordinated Collections of Microorganism/LMG
CCUG = Culture Collection, University of Göteborg (Sweden)
ATCC = American Type Culture Collection, Manassas, VA (USA)
BCCM/IHEM = Belgian Coordinated Collections of Microorganism/IHEM The cell densities were measured spectrophotometrically by optical density measurement (OD at 620 nm) for all of the strains, but only selected graphical results are included in FIGS. 1-4. All the strains, even those not shown in FIGS. 1-4, grew well when glucose was provided as the carbohydrate source. In contrast, for all strains, when cells were grown in basal medium (that contained only the equivalent amount of non-FOS carbohydrate present in the FOS powder), growth still occurred, but the final cell densities were significantly lower compared to the glucose-grown cells.

Figure 2:
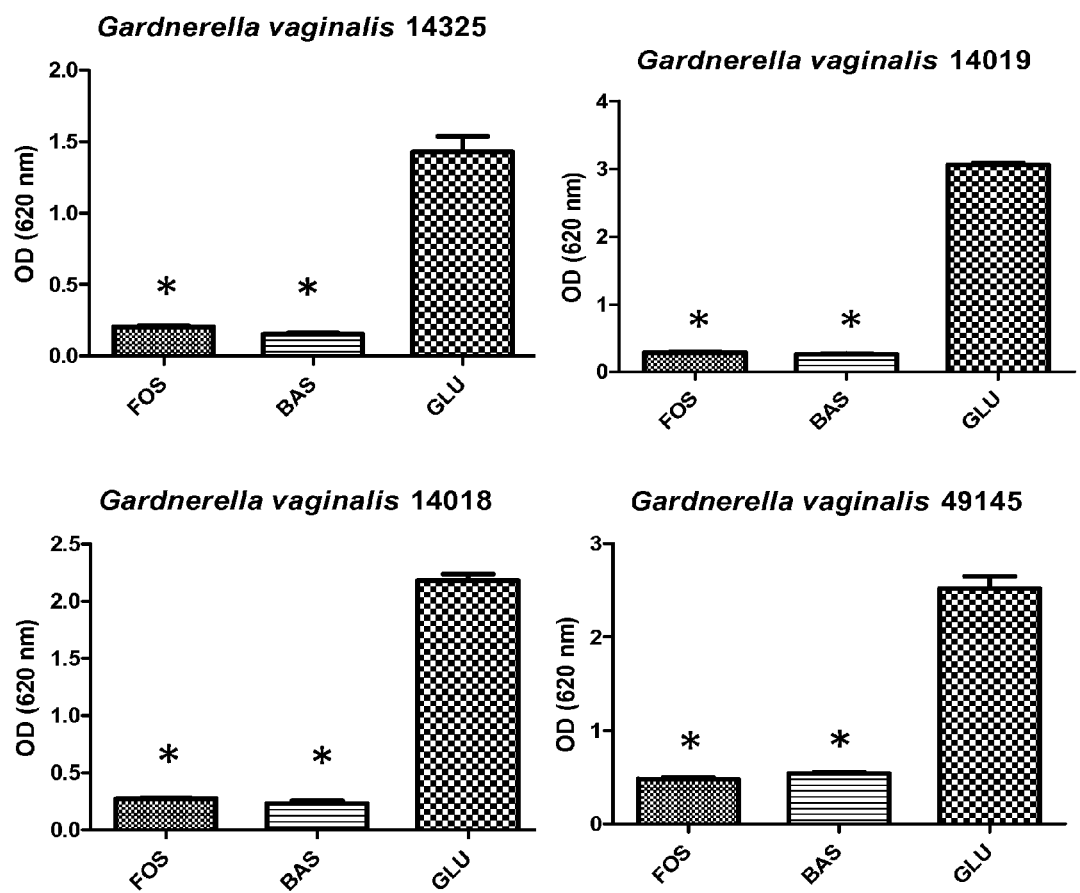
FIG. 2 contains four graphs showing that various strains of vaginal *Gardnerella vaginalis* do not grow in the presence of fructo-oligosaccharide.

Referring now to FIGS. 1-2, it can be seen that *Candida* and *Gardnerella* grew well when glucose was the carbohydrate source, but none of the *Candida* (four strains) and none of the *Gardnerella* (four strains) strains were able to ferment FOS. The growth on the FOS was essentially equivalent to the growth on the basal medium.

Figure 3:
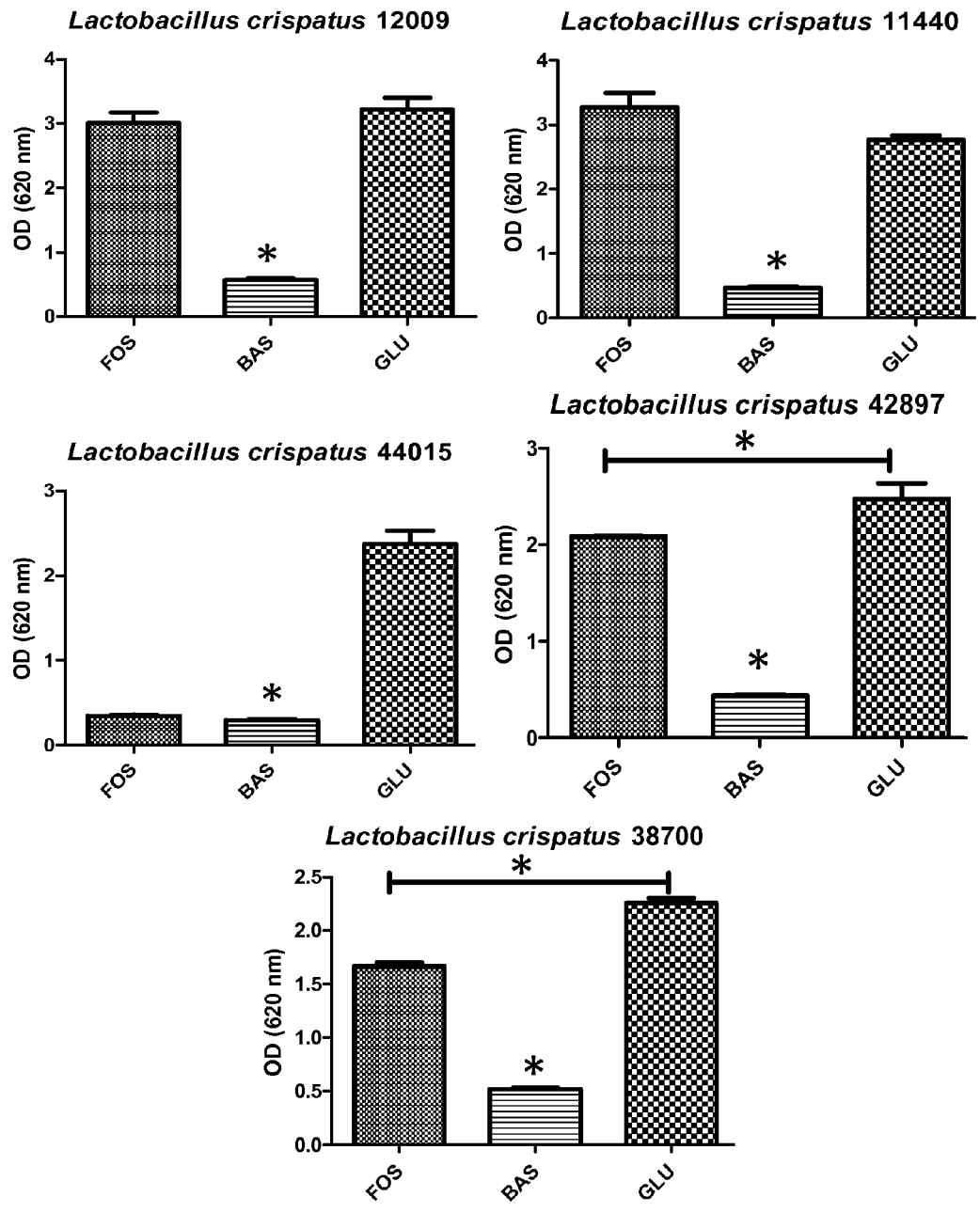
FIG. 3 contains five graphs showing that some strains of vaginal *Lactobacillus crispatus* do grow in the presence of fructo-oligosaccharide.
Figure 4:
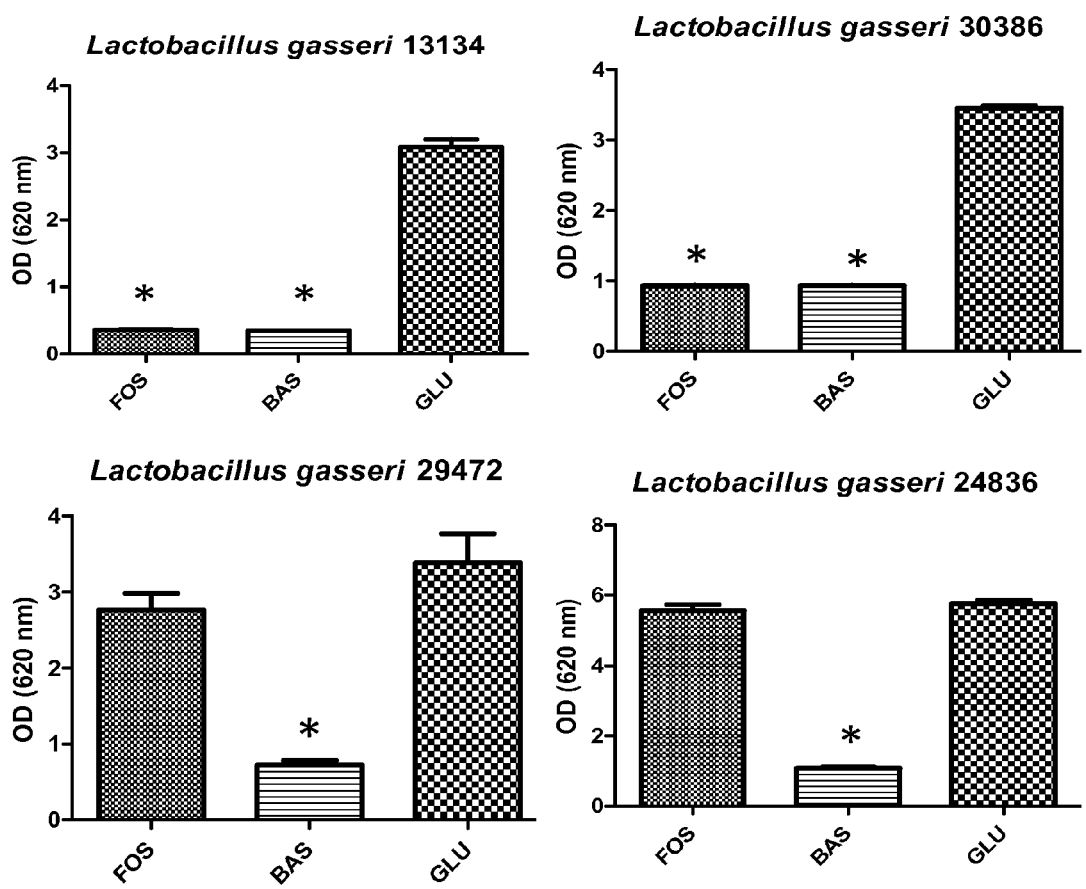
FIG. 4 contains four graphs showing that some strains of vaginal *Lactobacillus gasseri* do grow in the presence of fructo-oligosaccharide.

As shown in Table 2, only 6 strains of the 23 lactobacilli were able to grow on FOS. These included two strains of *Lactobacillus gasseri* and four strains of *Lactobacillus crispatus*. The growth of the remaining 17 tested strains on FOS followed the same pattern as on the basal medium, i.e., they were unable to use FOS as a carbohydrate source. As seen in FIGS. 3-4, although FOS utilization occurred by *Lactobacillus gasseri* and *Lactobacillus crispatus*, not all of their respective strains were FOS fermenters. With respect to *Lactobacillus crispatus*, in FIG. 3, strain 12009, strain 11440, strain 42897, and strain 38700 showed FOS fermentation at least about triple that of the basal medium and nearly as much FOS fermentation as the glucose medium. With respect to *Lactobacillus gasseri*, in FIG. 4, strain 29472 and strain 24836 showed FOS fermentation at least about triple that of the basal medium and nearly as much FOS fermentation as the glucose medium.

To confirm these results, the pH of the growth medium was measured after 24 hours for the FOS fermenters and non-fermenters. Sample results are shown below in Table 3 for one selected FOS fermenter and one selected non-FOS fermenter.

TABLE 3

|  | Fermentation | pH |
|---|---|---|
| FOS fermentor |  |  |
| *Lactobacillus crispatus* 38700 |  |  |
| MRS-glucose | Positive | 3.51 |
| MRS-FOS | Positive | 3.43 |
| MRS-basal | Negative | 5.50 |
| Non-FOS fermentor |  |  |
| *Lactobacillus iners* 18913 |  |  |
| MRS-glucose | Positive | 3.79 |
| MRS-FOS | Negative | 7.03 |
| MRS-basal | Negative | 7.11 |

Interestingly, the tests also show that no strains of opportunistic vaginal pathogens, such as *Gardnerella vaginalis* (a causative agent of bacterial vaginosis) and *Candida albicans* (the causative agent of vaginal candidiasis), grew on the FOS. Accordingly, the disclosed compositions having a prebiotic such as FOS will enhance the growth of at least some strains of native vaginal lactobacilli, provided that the vaginal environment was already colonized by the appropriate strains (i.e., FOS fermenters), but not the growth of opportunistic pathogens, which should promote healthy vaginal ecology.

In the examples that follow, the fructo-oligosaccharide used is a powder made by GTC Nutrition, of Golden, Colo. that is sold under the trade name NutraFlora P-95.

Example 2

Soft Gel Prebiotic Formulas

Softgel capsules are available as a regular beef soft gel or vegetarian softgel capsule.

|  | w/w % |
|---|---|
| Softgel Capsule Bovine | |
| Gelatin Beef skin | 30.4% |
| Gelatin Beef bone | 13.0% |
| Glycerin (99.5%) | 20.0% |
| Purified Water | 36.6% |
|  | 100% |
| Softgel Capsule Vegetarian | |
| Non-GMO Starch | 43.4% |
| Glycerin 99.5% | 25.0% |

-continued

| | w/w % |
|---|---|
| Carrageenan | 12.0% |
| Sorbitol | 10.0% |
| Purified Water | 9.6% |
| | 100% |

Both versions of the softgel capsule can be filled with the liquid prebiotic composition below.

| Liquid Prebiotic Filling for Soft Gels | |
|---|---|
| | w/w % |
| Propylene Glycol | 36.47% |
| Polyethylene glycol 1450 | 46.40% |
| Polyethylene glycol 400 NF | 5.50% |
| Glycerin 99.5% | 8.50% |
| Methylparaben | 0.10% |
| Fumed Silica | 1.00% |
| Lactic Acid | 0.03% |
| Fructo-oligosaccharide Powder | 2.00% |
| | 100% |

Large oval-shaped Soft gel capsules are formed, filled, and sealed around the "Prebiotic Filling" to a total weight of 2.8-3.2 grams each. Soft gels are packaged with a typical vaginal applicator that can be washed and re-used, or several single use applicators that can disposed of after each single use. Soft gels are also large enough as they could possibly be inserted with a finger if preferred.

Example 3

Formula A: Prebiotic Suppository containing Hydrogenated Vegetable Oil and Cocoa Butter

| Formula A | w/w % |
|---|---|
| Hydrogenated Vegetable Oil (Wecobee FS) | 90.44% |
| Deodorized cocoa butter NF | 5.80% |
| Tocopheryl acetate (Vitamin E) | 1.00% |
| Methylparaben | 0.18% |
| Propylparaben | 0.05% |
| Lactic acid | 0.03% |
| Fumed Silica | 0.50% |
| Fructo-oligosaccharide Powder | 2.00% |
| | 100.00% |

Formula B: Prebiotic Suppository containing Hydrogenated Vegetable Oil and Cocoa Butter

| Formula B | w/w % |
|---|---|
| Deodorized cocoa butter NF | 85.10% |
| Hydrogenated Vegetable Oil (Wecobee M) | 6.14% |
| Glyceryl Monostearate | 5.00% |
| Tocopheryl acetate (Vitamin E) | 1.00% |
| Methylparaben | 0.18% |
| Propylparaben | 0.05% |
| Lactic acid | 0.03% |
| Fumed Silica | 0.50% |
| Fructo-oligosaccharide Powder | 2.00% |
| | 100.00% |

Formulas with the hydrogenated vegetable oil and cocoa butter are made by melting the raw materials in a hotbox before blending with the fructo-oligosaccharide and the suspending agent. Molten material is then transported to the suppository filling machine where the suppositories are formed and filled to 1.9-2.1 grams each. A plastic applicator is typically used for insertion.

Example 4

Hard Gelatin Capsules Prebiotic Formulation

Gelatin capsules are purchased as empty halves and are available in bovine or vegetarian formulas as industry standards. The percentage of gelatin can be adjusted so the insert remains firm for application, but dissolves at body temperature. The halves are filled with the 1.5-2.0 grams of free flowing powder and closed together to make gelatin capsules of various sizes. They can be sealed or remain movable as they slide together, but for this application the two halves sealed together with the typical method would be preferable. The capsules can be inserted with a plastic applicator or finger.

| Formula | w/w % |
|---|---|
| Fructo-oligosaccharide Powder | 4.0% |
| Calcium phosphate | 4.45% |
| Magnesium stearate | 2.0% |
| Rice Flour or Maize starch | 89.0% |
| Silicon dioxide | 0.75% |
| Citric acid | 0.05% |
| | 100.00% |

Example 5

The Prebiotic raw material, fructo-oligosaccharide may also be pressed into a tablet for insertion with an applicator. Standard tabletting techniques utilizing granulating and milling are used to provide a smooth slow-dissolving tablet of approximately 980-1080 milligrams each. The typical formula follows.

| Tablet - Formula A | w/w % |
|---|---|
| Microcrystalline cellulose | 45.6 |
| Dicalcium phosphate dihydrate | 45.8 |
| A disintegrant | 3.0 |
| A lubricant | 1.0 |
| Fumed silica | 0.5 |
| Ascorbic acid | 0.1 |
| Fructo-oligosaccharide Powder | 4.0 |
| | 100.0% |

| Tablet - Formula B | w/w % |
|---|---|
| Lactose monohydrate | 58.9 |
| Hydroxypropyl methylcellulose | 6.0 |
| Microcrystalline cellulose | 27.0 |
| A lubricant | 1.00 |
| Ascorbic acid | 0.10 |
| A disintegrant | 3.00 |
| Fructo-oligosaccharide Powder | 4.0 |
| | 100% |

The lubricant may be any known tabletting lubricant compatible with the formulation. Suitable tabletting lubricants include, but are not limited to, magnesium stearate, hydrogenated vegetable oil, sodium stearyl fumarate, or combinations thereof.

The disintegrant may be any known tabletting disintegrant compatible with the formulation. Suitable tabletting disintegrants include, but are not limited to, sodium starch glycolate, soy polysaccharides, croscarmellose sodium, and combinations thereof.

The embodiments of this invention described in detail and by reference to specific exemplary embodiments of the prebiotic containing compositions are within the scope of the appended claims. It is contemplated that numerous other modifications and variations of the compositions may be created taking advantage of the disclosed approach. In short, it is the applicants' intention that the scope of the patent issuing herefrom be limited only by the scope of the appended claims.

What is claimed is:

1. A vaginal suppository for vaginal health maintenance consisting essentially of:
    about 2-10% by weight of a dry prebiotic suspended in a suppository base by about 0.5-1.5% weight of a dry inorganic suspending agent in the form of a solid at room temperature that melts at about 94° F. to about 100° F.; and
    about 0.01-0.04% by weight of a weak acid;
    wherein the balance of the vaginal suppository is the suppository base;
    wherein the vaginal health maintenance entails promotion of the growth of strains of native vaginal flora *Lactobacillus gasseri* and *Lactobacillus crispatus* that ferment the prebiotic, but does not promote the growth of *Gardenerella vaginalis* and *Candida albicans*;
    wherein the composition is essentially free of probiotics, lactoferrin, and plant extracts containing isoflavones, and is free of water and therapeutic agents;
    wherein the prebiotic is a bifidogenic oligosaccharide selected from the group consisting of fructo-oligosaccharide, galacto-oligosaccharide, inulin, isomalto-oligosaccharide, lactulose, soy-oligosaccharide, xylo-oligosaccharide, and combinations thereof.

2. The vaginal suppository of claim 1 further consists essentially of a preservative as about 0.1-0.18% by weight of the suppository.

3. The vaginal suppository of claim 1 wherein the inorganic suspending agent comprises silicon dioxide.

4. The vaginal suppository of claim 1 wherein the suppository base comprises a polyethylene glycol.

5. The vaginal suppository of claim 1 wherein the prebiotic includes fructo-oligosaccharide.

6. The vaginal suppository of claim 1 wherein the suppository base includes polyethylene glycol, the prebiotic is fructo-oligosaccharide, and further consists essentially of a preservative.

7. The vaginal suppository of claim 6 wherein the polyethylene glycol is about 97% by weight of the composition and the fructo-oligosaccharide is about 2% by weight of the composition.

8. The vaginal suppository of claim 6 wherein the polyethylene glycol comprises a mixture of polyethylene glycol 1000 and polyethylene glycol 1450.

9. The vaginal suppository of claim 6 wherein the preservative includes methylparaben and is about 0.1% by weight of the composition; the inorganic suspending agent includes silicon dioxide and is about 0.8% by weight of the composition; and the pH adjuster includes lactic acid and is about 0.03% by weight of the composition.

10. A method for promoting vaginal health maintenance by the growth of native vaginal flora, the method comprising:
    inserting a vaginal suppository into a vagina, the vaginal suppository consisting essentially of:
        about 2-10% by weight of a dry prebiotic suspended in a suppository base by about 0.5-1.5% weight of a dry inorganic suspending agent in the form of a solid at room temperature that melts at about 94° F. to about 100° F.; and
        about 0.01-0.04% by weight of a weak acid;
        wherein the balance of the vaginal suppository is the suppository base, the vaginal suppository is essentially free of probiotics, lactoferrin, and plant extracts containing isoflavones, and is free of water and therapeutic agents;
        wherein the prebiotic is a bifidogenic oligosaccharide selected from the group consisting of fructo-oligosaccharide, galacto-oligosaccharide, inulin, isomalto-oligosaccharide, lactulose, soy-oligosaccharide, xylo-oligosaccharide, and combinations thereof; and
    allowing at least some strains of native vaginal flora *Lactobacillus gasseri* and vaginal *Lactobacillus crispatus* to ferment the prebiotic thereby promoting the growth of said strains, but not the growth of *Gardenerella vaginalis* and *Candida albicans*, such that vaginal health maintenance is promoted.

11. The method of claim 10 wherein the vaginal suppository helps prevent bacterial vaginosis.

12. The method of claim 10 wherein the allowing step includes allowing about five to eight hours to elapse.

13. The method of claim 10 wherein the inserting step and the allowing steps are repeated once daily.

14. The method of claim 10 wherein the inorganic suspending agent comprises silicon dioxide.

15. The method of claim 10 wherein the suppository base comprises a polyethylene glycol.

16. The method of claim 10 wherein the prebiotic includes fructo-oligosaccharide.

17. The method of claim 10 wherein the suppository base includes polyethylene glycol and the prebiotic is fructo-oligosaccharide.

18. The method of claim 17 wherein the polyethylene glycol is about 97% by weight of the composition and the fructo-oligosaccharide is about 2% by weight of the composition.

19. The method of claim 17 wherein the polyethylene glycol comprises a mixture of polyethylene glycol 1000 and polyethylene glycol 1450.

20. The method of claim 10 wherein the inorganic suspending agent includes silicon dioxide and is about 0.8% by weight of the composition; and the pH adjuster includes lactic acid and is about 0.03% by weight of the composition, and the vaginal suppository further consists essentially of a preservative at about 0.1% by weight of the composition.

* * * * *